United States Patent
Yamin et al.

(10) Patent No.: US 11,944,781 B2
(45) Date of Patent: Apr. 2, 2024

(54) INTRAVENOUS FILTER WITH PRIMING FUNCTION

(71) Applicant: CareFusion 303. Inc., San Diego, CA (US)

(72) Inventors: Leyla Yamin, San Diego, CA (US); Kelly Kloster Hon, Del Mar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 382 days.

(21) Appl. No.: 17/223,938

(22) Filed: Apr. 6, 2021

(65) Prior Publication Data
US 2022/0313903 A1 Oct. 6, 2022

(51) Int. Cl.
*A61M 5/165* (2006.01)
*A61M 39/08* (2006.01)
*A61M 39/24* (2006.01)
*A61M 5/14* (2006.01)

(52) U.S. Cl.
CPC ............ *A61M 5/165* (2013.01); *A61M 39/08* (2013.01); *A61M 39/24* (2013.01); *A61M 2005/1402* (2013.01); *A61M 2039/2446* (2013.01)

(58) Field of Classification Search
CPC ............ A61M 5/1411; A61M 5/16881; A61M 5/16804; A61M 2005/1402; A61M 2039/224; A61M 2039/229; A61M 2039/2473; A61M 2039/248; A61M 2039/2486; A61M 2039/2493; A61M 39/223; A61M 39/22; A61M 39/24
See application file for complete search history.

(56) References Cited

U.S. PATENT DOCUMENTS

| 4,009,714 A | 3/1977 | Hammer |
| 4,046,696 A * | 9/1977 | Mouwen .............. B01D 35/147 210/431 |

OTHER PUBLICATIONS

International Search Report and Written Opinion in Application No. PCT/US2022/022383, dated Jul. 19, 2022, 17 pages.

* cited by examiner

*Primary Examiner* — Nathan R Price
*Assistant Examiner* — Anh Bui
(74) *Attorney, Agent, or Firm* — Morgan, Lewis & Bockius LLP

(57) ABSTRACT

IV filters are described herein. An IV filter includes a filter housing, a filter media, a filter channel, a priming channel, and a disk valve. The filter housing defines an inlet and an outlet. The filter media is disposed within the filter housing. The filter channel is disposed within the filter housing. The filter channel is in fluid communication with the inlet and the filter media, and the filter media permits flow from the filter channel to the outlet and captures particulate from the flow. The priming channel is disposed within the filter housing. The priming channel is in fluid communication with the inlet and the outlet. The disk valve is coupled to the filter housing. The disk valve is moveable to direct flow from the inlet to the priming channel in a first position and to direct flow from the inlet to the filter channel in a second position.

12 Claims, 4 Drawing Sheets

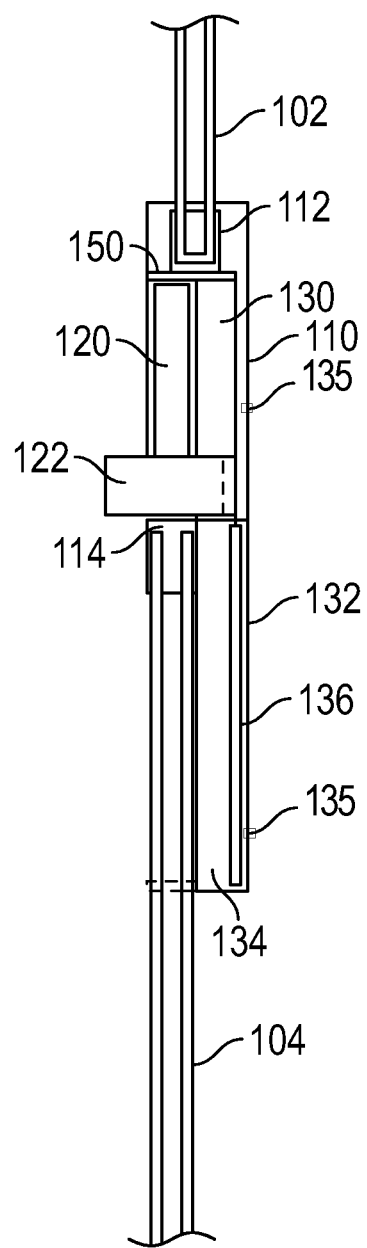
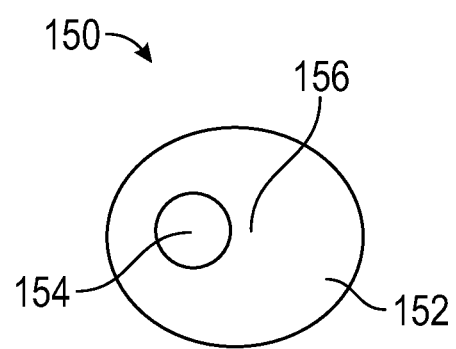
FIG. 5
FIG. 4

INTRAVENOUS FILTER WITH PRIMING FUNCTION

FIELD OF THE INVENTION

The present disclosure generally relates to filters, and, in particular, to filters for intravenous sets.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. During operation, medical fluid can be filtered to prevent the transfer of bacteria, microorganisms, and/or other pathogens.

In some applications, filters can require a significant amount of time to prime with fluid, delaying certain procedures.

SUMMARY

The disclosed subject matter relates to IV filters. In certain embodiments, an IV filter is disclosed that comprises a filter housing defining an inlet and an outlet; a filter media disposed within the filter housing; a filter channel disposed within the filter housing, wherein the filter channel is in fluid communication with the inlet and the filter media, and the filter media permits flow from the filter channel to the outlet and captures particulate from the flow; a priming channel disposed within the filter housing, wherein the priming channel is in fluid communication with the inlet and the outlet; and a disk valve coupled to the filter housing, wherein the disk valve is moveable to direct flow from the inlet to the priming channel in a first position and to direct flow from the inlet to the filter channel in a second position.

In certain embodiments, a method is disclosed that comprises introducing flow to an IV filter; directing flow from an inlet of the IV filter to an outlet of the IV filter via a priming channel to bypass a filter media; moving a disk valve to direct flow from the priming channel to a filter channel; and directing flow from the inlet through a filter media via the filter channel.

In certain embodiments, an IV set is disclosed that comprises a first portion of tubing; a second portion of tubing; and an IV filter comprising: a filter housing defining an inlet in fluid communication with the first portion of tubing and an outlet in fluid communication with the second portion of tubing; a priming channel disposed within the filter housing, wherein the priming channel is in fluid communication with the first portion of tubing and the second portion of tubing; a filter media disposed within the filter housing; a filter channel disposed within the filter housing, wherein the filter channel is in fluid communication with the first portion of tubing and the filter media, and the filter media permits flow from the filter channel to the second portion of tubing and captures particulate from the first portion of tubing; and a disk valve coupled to the filter housing, wherein the disk valve is moveable to direct flow from the first portion of tubing to the priming channel in a first position and to direct flow from the first portion of tubing to the filter channel in a second position.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4 illustrates a side cross-sectional schematic view of the in-line IV filter of FIG. 2.

FIG. 5 illustrates a top view of a disk valve of the in-line IV filter of FIG. 2.

DETAILED DESCRIPTION

The disclosed IV filter provides a priming flow path, a filter flow path, and a valve to direct flow between the priming flow path and the filter flow path. The IV filter selectively allows for rapid priming of the filter and filtration of medical fluid.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the filters for the administration of medical fluid using the disclosed IV filter, it is to be understood that this description is only an example of usage and does not limit the scope of the claims. Various aspects of the disclosed filter may be used in any application where it is desirable to provide rapid priming of an IV filter.

The disclosed in-line IV filter overcomes several challenges discovered with respect to certain conventional in-line IV filters. One challenge with certain conventional in-line IV filters is that certain conventional in-line IV filters may require a significant amount of time to draw in sufficient medical fluid to prime the in-line IV filter. Another challenge with certain conventional in-line IV filters is that certain conventional in-line IV filters can become clogged with extended or prolonged use. Because significant priming time may delay procedures and occupy a clinician's attention, and clogged filters can reduce filtration efficiency and filter life, the use of conventional in-line IV filter is not desirable.

Therefore, in accordance with the present disclosure, it is advantageous to provide an in-line IV filter as described herein that allows for rapid priming. Further, it is advantageous to provide an in-line IV filter as described herein that limits flow through the filter to extend the life of the filter media.

Examples of IV filters that allow for rapid priming and extend the life of the filter media are now described.

Figure 1:
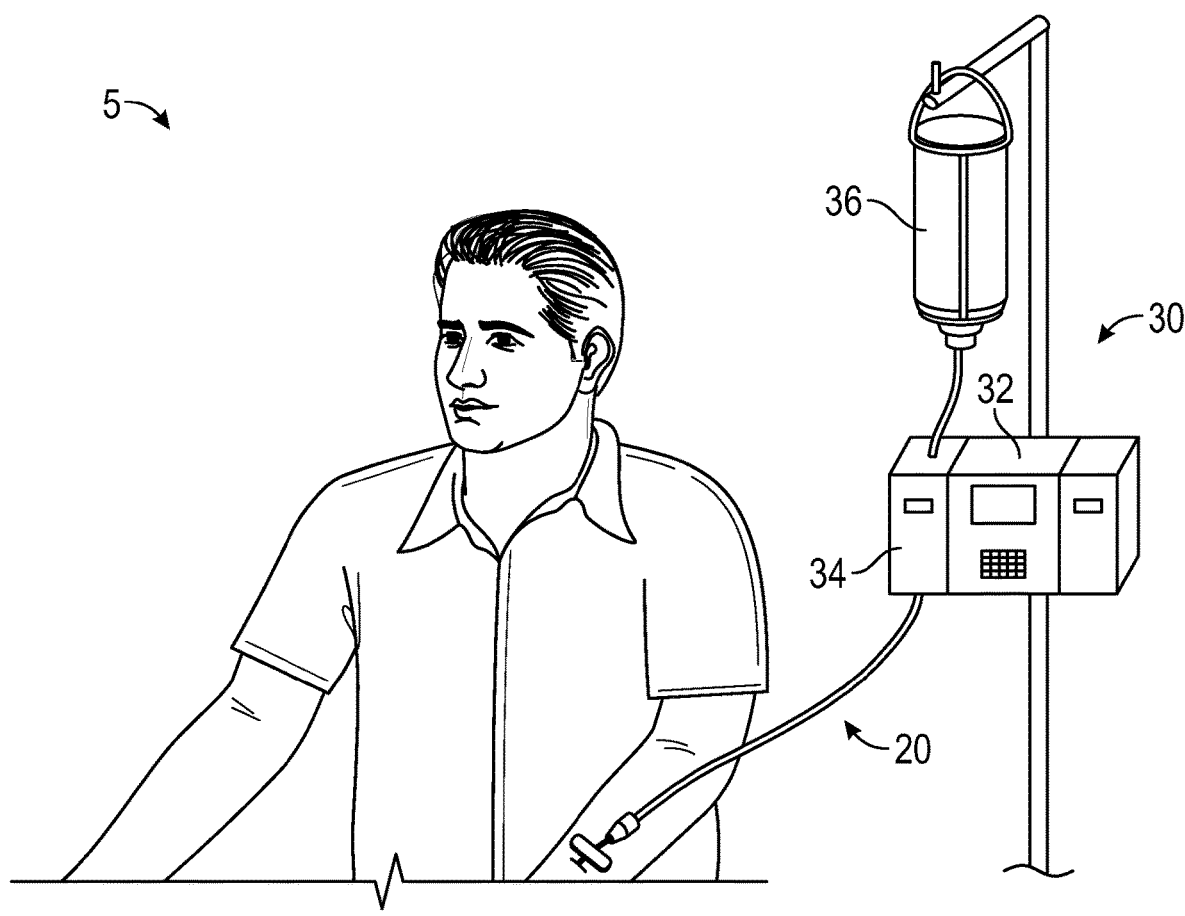
FIG. 1 illustrates a patient receiving an infusion of a medical fluid through an IV pump according to certain aspects of the present disclosure.

FIG. 1 illustrates a patient 5 receiving an infusion of a medical fluid through an IV pump 30 according to certain aspects of the present disclosure. The IV pump 30 comprises a controller 32 and two pump modules 34. An IV set 20 is connected between a container 36 of the medical fluid and the patient 5. Prior to operation, components of the IV set 20 can be primed with medical fluid. Further, during operation, medical fluid delivered to the patient 5 can be filtered to prevent the transfer of bacteria, microorganisms, and/or other pathogens. An in-line IV filter as described herein can allow for priming operations and filtration of the medical fluid delivered to the patient 5. In some embodiments, an in-line IV filter assembly can be disposed in between or in line with tubing of the IV set 20. As can be appreciated, an in-line IV filter can be utilized with other assemblies, such as gravity sets.

Figure 2:
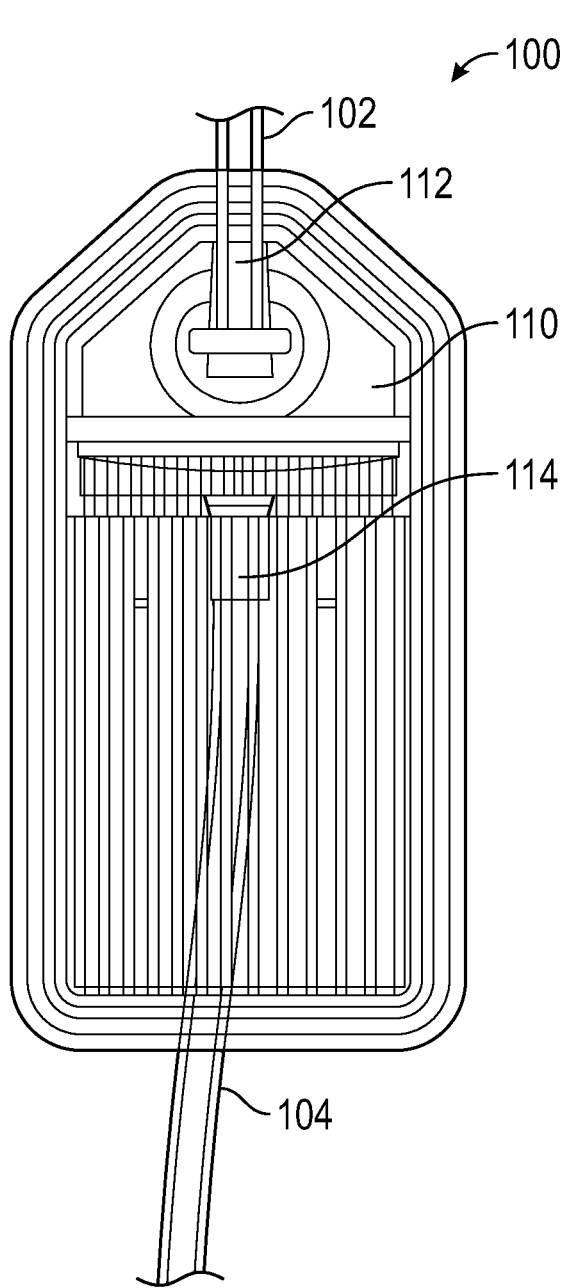
FIG. 2 illustrates a front view of an in-line IV filter according to certain aspects of the present disclosure.
Figure 3:
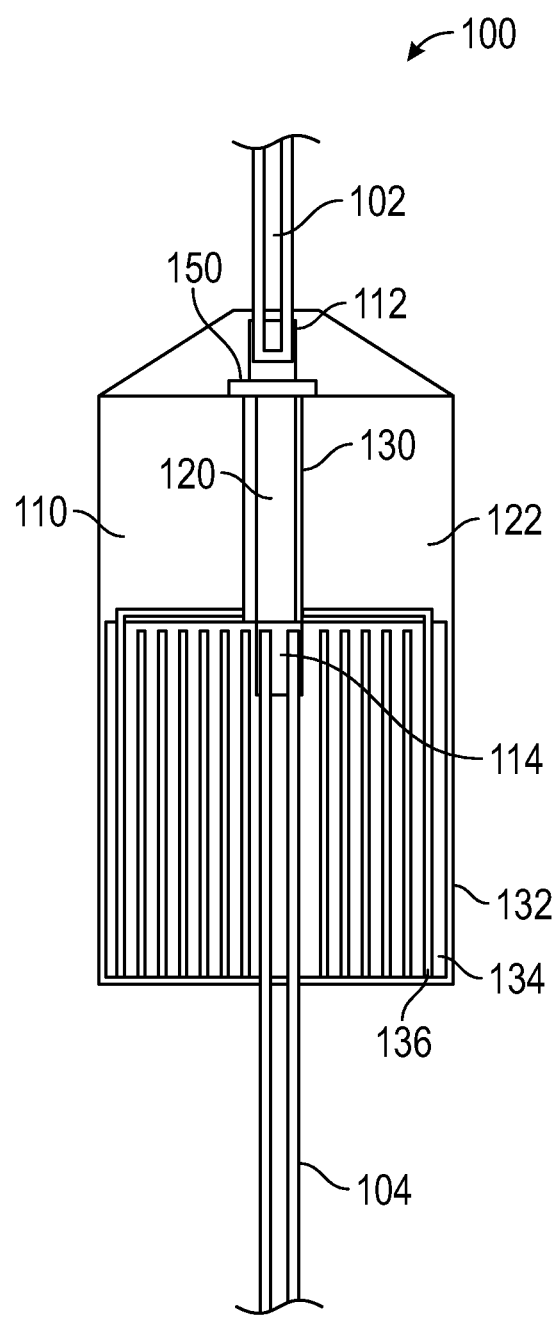
FIG. 3 illustrates a front cross-sectional view of the in-line IV filter of FIG. 2.

FIG. 2 illustrates a front view of an in-line IV filter 100 according to certain aspects of the present disclosure. FIG. 3 illustrates a front cross-sectional view of the in-line IV filter 100 of FIG. 2. FIG. 4 illustrates a side cross-sectional view of the in-line IV filter 100 of FIG. 2. With reference to FIGS. 2-4, the in-line IV filter 100 allows for filtration of fluids through an IV set.

In the depicted example, fluid flow enters the in-line IV filter 100 through an inlet 112 formed in a body 110 of the in-line IV filter 100. The inlet 112 provides fluid communication with a volume defined within the body 110 to allow the medical fluid to be filtered. The body 110 can be formed from a rigid material, including, but not limited to plastic.

In some embodiments, tubing 102 from the IV set 20 can be coupled to the inlet 112 to allow flow from a fluid container 36 or other component of the IV set 20 into the volume defined within the body 110. The fluid flow can have a positive pressure to pass through the in-line IV filter 100.

In the depicted example, fluid flow from the inlet 112 can be directed to the filter media 134 through a filter channel 130 disposed within the body 110. The filter channel 130 can define a flow path from the inlet 112 toward the filter media 134.

As illustrated, fluid from the filter channel 130 can pass through the filter media 134 to prevent the transfer of bacteria, microorganisms, and/or other pathogens to the patient. Further, fluid can pass through the filter media 134 to eliminate air from the medical fluid through one or more air vents 135. During operation, fluid can flow from the filter channel 130 through the filter media 134 to a reservoir 122 formed within the body 110. As can be appreciated, a positive pressure differential can direct fluid flow from the filter channel 130 through the filter media 134 to the reservoir 122.

As described herein, the filter media 134 can selectively filter the flow through the in-line IV filter 100. The filter media 134 can have a generally planar or rectangular prism shape. In some embodiment, the filter media 134 can be round or any other suitable shape. As illustrated, the filter media 134 can extend along a portion of the width and length of the body 110. In some embodiments, the filter media 134 can extend generally along the width of the body 110. During operation, fluid flow can flow into the filter media 134 along the surface area of the filter media 134 exposed to the flow from the filter channel 130.

As illustrated, the filter media 134 can be supported by portions of the body 110. In some embodiments, portions of the filter media 134 can be captured between opposing portions of the body 110. Optionally, protrusions or filter supports 136 formed in the body 110 can further retain or support the filter media 134 within the body 110.

In some embodiments, the filter supports 136 can define one or more filter flow paths 132 from the filter channel 130 into the filter media 134. As illustrated, the filter flow paths 132 can be defined between adjacent filter supports 136 within the body 110. During operation, fluid can flow from the filter channel 130, along one or more filter flow paths 132 and into the filter media 134. Optionally, the filter flow paths 132 defined by the filter supports 136 can include tortuous flow paths or flow paths with a plurality of turns. For example, the filter flow paths 132 can extend along a length of the wall of the filter 100 and then directed back in an adjacent opposite path.

After passing through the filter media 134, the fluid flow can exit the in-line IV filter 100 through an outlet 114 formed in a body 110 of the in-line IV filter 100. Similar to the inlet 112, in some embodiments, tubing 104 from the IV set 20 can be coupled to the outlet 114 to allow flow from the in-line IV filter 100 to the patient or other components of the IV set 20.

Optionally, fluid passing through the filter media 134 can be stored or retained within a reservoir 122 defined within the body 110. During operation, fluid within the reservoir 122 can be accumulated and dispensed based on fluid delivery conditions and demands. In the depicted example, fluid flow can exit the in-line IV filter 100 through the outlet 114 in fluid communication with the reservoir 122.

Further, in the depicted example, the in-line IV filter 100 can bypass the filter media 134 to facilitate priming operations. As can be appreciated, by bypassing the filter media 134, the in-line IV filter 100 can by rapidly primed and the life of the filter media 134 can be extended by avoiding unnecessary filtering of the priming fluid flow.

During priming, the in-line IV filter 100 can allow for medical fluid to flow from the inlet 112 to the outlet 114 without passing through the filter media 134, allowing fluid to pass through the in-line IV filter 100 at a greater rate compared to fluid flow that is directed through the filter media 134. In the depicted example, the medical fluid can flow from the inlet 112 to the outlet 114 via a priming channel 120. In some embodiments, medical fluid can flow the inlet 112 to the reservoir 122 via the priming channel 120. Fluid can exit the in-line IV filter 100 through the outlet 114 in fluid communication with the reservoir 122. As can be appreciated, the inner diameter of the priming channel 120 can be larger than the inner diameter of the channels that direct flow through the filter media 134, allowing for flow through the priming channel 120 to flow faster than flow through the filter flow path.

In the depicted example, the in-line IV filter 100 can be configured to allow for filtration of medical fluid during normal operation and for increased priming flow during priming operations or any other air elimination operations during IV therapy. FIG. 5 illustrates a top view of a disk valve 150 of the in-line IV filter 100 of FIG. 2. With reference to FIGS. 2-5, the disk valve 150 can direct flow from the inlet 112 to the filter channel 130 for filtering operation or to the priming channel 120 for priming operation.

During operation, the disk valve 150 is movable to direct flow from the inlet 112 toward the filtering channel 130 or the priming channel 120. As illustrated, the disk valve 150 defines a flow portion 154 that permits flow to pass therethrough. The flow portion 154 can be shaped or otherwise configured to direct flow from the inlet 112 toward the filtering channel 130 and/or the priming channel 120. The disk valve 150 further defines a seal portion 152 that is shaped to prevent or block flow from the inlet 112 to the filtering channel 130 and/or the priming channel 120.

In the depicted example, the flow portion 154 and the seal portion 152 of the disk valve 150 can be moved or aligned to control the flow from the inlet 112 and the operation of the in-line IV filter 100.

Figure 6A:
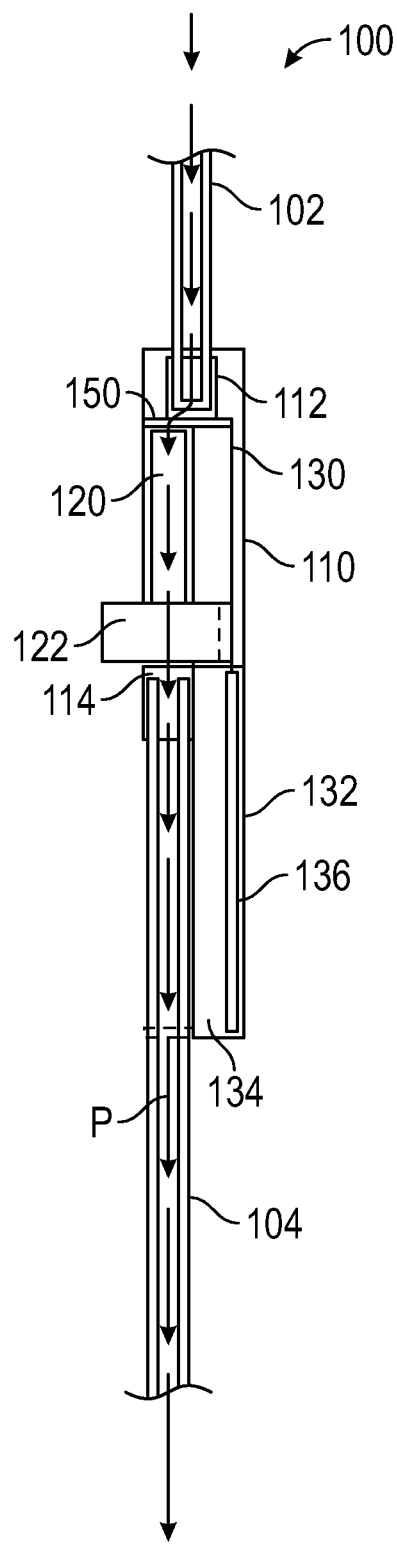
FIG. 6A illustrates a side cross-sectional schematic view of the in-line IV filter of FIG. 2 in a priming configuration.

FIG. 6A illustrates a side cross-sectional schematic view of the in-line IV filter 100 of FIG. 2 in a priming configuration. With reference to FIGS. 2-6A, the disk valve 150 can be moved to allow the in-line IV filter 100 to operate in a priming configuration. In the depicted example, the disk valve 150 can be moved to align the flow portion 154 to direct flow from the inlet 112 toward the priming channel 120. As illustrated, the flow portion 154 can direct flow from the inlet 112 through the priming channel 120 to the outlet 114, permitting priming flow P to bypass the filter media 134 and pass through the in-line IV filter 100. Further, the seal portion 152 can be aligned to prevent flow from the inlet 112 toward the filtering channel 130. As illustrated, the seal portion 152 can seal the filtering channel 130 to prevent flow from the inlet 112 from entering the filter media 134.

Figure 6B:
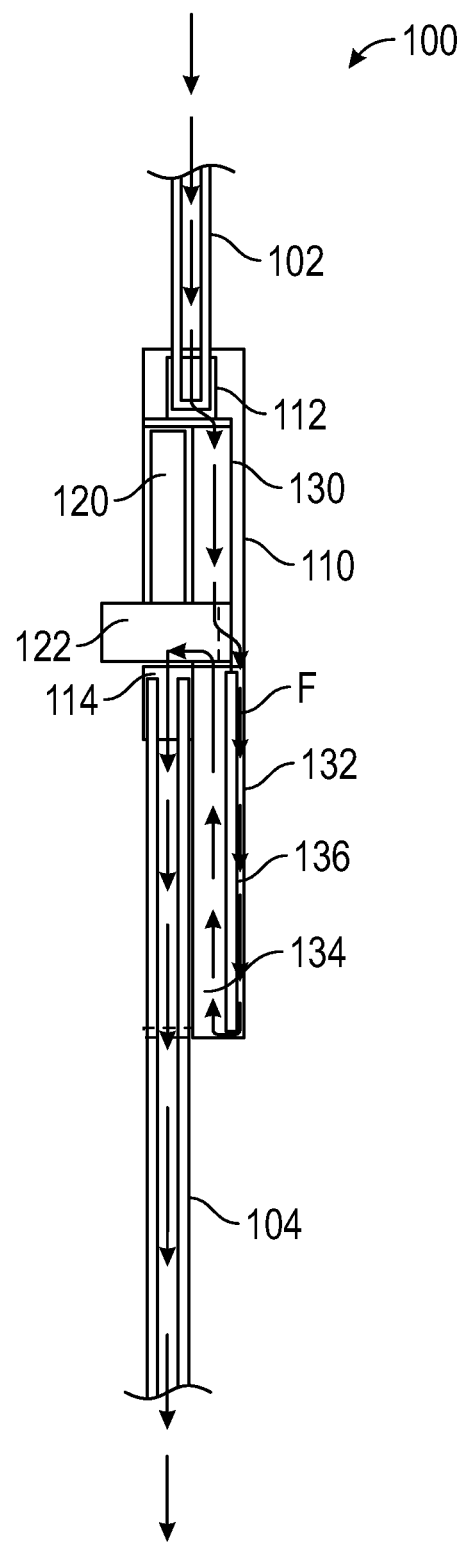
FIG. 6B illustrates a side cross-sectional schematic view of the in-line IV filter of FIG. 2 in a filtering configuration.

FIG. 6B illustrates a side cross-sectional schematic view of the in-line IV filter 100 of FIG. 2 in a filtering configuration. With reference to FIGS. 2-5 and 6B, the disk valve 150 can be moved to allow the in-line IV filter 100 to operate in a filtering configuration. In the depicted example, the disk valve 150 can be moved to align the flow portion 154 to direct flow from the inlet 112 toward the filtering channel 130. As illustrated, the flow portion 154 can direct flow from the inlet 112 through the filtering channel 130 to the filter media 134, permitting filter flow F to pass through the filter media 134. Further, the seal portion 152 can be aligned to prevent flow from the inlet 112 toward the priming channel 120. As illustrated, the seal portion 152 can seal the priming channel 120 to prevent flow from the inlet 112 from bypassing the filter media 134.

As described herein, the disk valve 150 can be moved to change the in-line IV filter 100 between the filtering configuration and the priming configuration. The disk valve 150 can be slid, rotated, or otherwise actuated to adjust the position of the disk valve 150. In some embodiments, the disk valve 150 is rotatable relative to the body 110. Optionally, an outer portion 156 of the disk valve 150 can be rotated to move or otherwise actuate the disk valve 150 and adjust the position of the flow portion 154 and/or the seal portion 152 of the disk valve 150.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An IV filter, comprising:
a filter housing defining an inlet and an outlet;
a filter media disposed within the filter housing;
a filter channel disposed within the filter housing, wherein the filter channel is in fluid communication with the inlet and the filter media, and the filter media permits flow from the filter channel to the outlet and captures particulate from the flow;
a priming channel disposed within the filter housing, wherein the priming channel is in fluid communication with the inlet and the outlet; and
a disk valve coupled to the filter housing, wherein the disk valve defines a flow portion configured to permit flow therethrough and a seal portion configured to prevent flow therethrough and the disk valve is moveable to (i) direct flow from the inlet to the filter channel in a first position and (ii) to align the flow portion of the disk valve with the priming channel to direct flow from the inlet to the priming channel and to align the seal portion of the disk valve with the filter channel to obstruct flow to the filter channel in a second position.

2. The IV filter of claim 1, wherein the priming channel is configured to direct flow from the inlet to the outlet at a first flow rate, the filter channel is configured to direct flow from the inlet to the outlet at a second flow rate, and the first flow rate is greater than the second flow rate.

3. The IV filter of claim 1, wherein the flow portion is aligned with the filter channel to permit fluid communication between the inlet and the filter channel and the seal portion is aligned with the priming channel to prevent fluid communication between the inlet and the priming channel in the first position.

4. The IV filter of claim 1, wherein the disk valve comprises an outer portion disposed around the flow portion and the seal portion, configured to permit a user to move the disk valve.

5. The IV filter of claim 1, wherein the flow portion and the seal portion of the disk valve are rotatable relative to the filter housing.

6. The IV filter of claim 1, further comprising a reservoir in fluid communication with the outlet.

7. The IV filter of claim 6, wherein the priming channel is in fluid communication with the reservoir.

8. The IV filter of claim 6, wherein the filter media is in fluid communication with the reservoir.

9. The IV filter of claim 1, further comprising at least one filter support to support the filter media within the filter housing.

10. An IV set, comprising:
a first portion of tubing;
a second portion of tubing; and
an IV filter, comprising:
a filter housing defining an inlet in fluid communication with the first portion of tubing and an outlet in fluid communication with the second portion of tubing;
a priming channel disposed within the filter housing, wherein the priming channel is in fluid communication with the first portion of tubing and the second portion of tubing;
a filter media disposed within the filter housing;
a filter channel disposed within the filter housing, wherein the filter channel is in fluid communication with the first portion of tubing and the filter media, and the filter media permits flow from the filter channel to the second portion of tubing and captures particulate from the first portion of tubing; and
a disk valve coupled to the filter housing, wherein the disk valve the disk valve defines a flow portion configured to permit flow therethrough and a seal portion configured to prevent flow therethrough and is moveable to (i) direct flow from the first portion of tubing to the filter channel in a first position and (ii) to align the flow portion of the disk valve with the priming channel to direct flow from the first portion of tubing to the priming channel and to align the seal portion of the disk valve with the filter channel to obstruct flow to the filter channel in a second position.

11. The IV set of claim 10 wherein the priming channel is configured to direct flow from the first portion of tubing to the second portion of tubing at a first flow rate, the filter channel is configured to direct flow from the first portion of tubing to the second portion of tubing at a second flow rate, and the first flow rate is greater than the second flow rate.

12. The IV set of claim 10, wherein the flow portion is aligned with the filter channel to permit fluid communication between the first portion of tubing and the filter channel and the seal portion is aligned with the priming channel to prevent fluid communication between the first portion of tubing and the priming channel in the first position.

* * * * *